United States Patent [19]

Adams Theodore P. et al.

[11] Patent Number: 5,336,245
[45] Date of Patent: Aug. 9, 1994

[54] STORAGE INTERROGATION APPARATUS FOR CARDIAC DATA

[75] Inventors: Adams Theodore P., Edina; Mark W. Kroll, Minnetonka, both of Minn.

[73] Assignee: Angeion Corporation, Plymouth, Minn.

[21] Appl. No.: 886,325

[22] Filed: May 20, 1992

[51] Int. Cl.⁵ .............................................. A61N 1/02
[52] U.S. Cl. ...................................... 607/32; 128/904
[58] Field of Search ............ 128/419 D, 419 PT, 696, 128/697, 910, 903, 904; 607/32

[56] References Cited

U.S. PATENT DOCUMENTS

| | | | |
|---|---|---|---|
| 4,295,474 | 10/1981 | Fischell | 128/419 D |
| 4,305,397 | 12/1981 | Weisbrod et al. | 128/419 PT |
| 4,531,527 | 7/1985 | Reinhold, Jr. et al. | 128/903 |
| 4,794,532 | 12/1988 | Leckband et al. | 128/710 |
| 4,809,697 | 3/1989 | Causey et al. | 128/419 PT |
| 5,107,862 | 4/1992 | Fabian et al. | 128/903 |

*Primary Examiner*—William E. Kamm
*Attorney, Agent, or Firm*—Joel D. Skinner

[57] ABSTRACT

A storage interrogation apparatus for communication with an implanted medical device and with remote communications systems. The apparatus comprises a microprocessor for implementing program control instructions, an RF receiver/transmitter connected to the microprocessor for transmitting and receiving signals between the interrogator and the implanted medical device, a memory integrated circuit for storing signal data received from the implanted medical device, and a transmission system for transmitting stored signal data to a location remote from the interrogator.

14 Claims, 3 Drawing Sheets

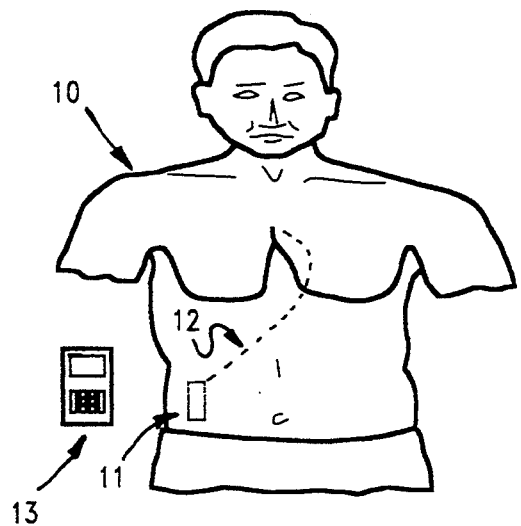
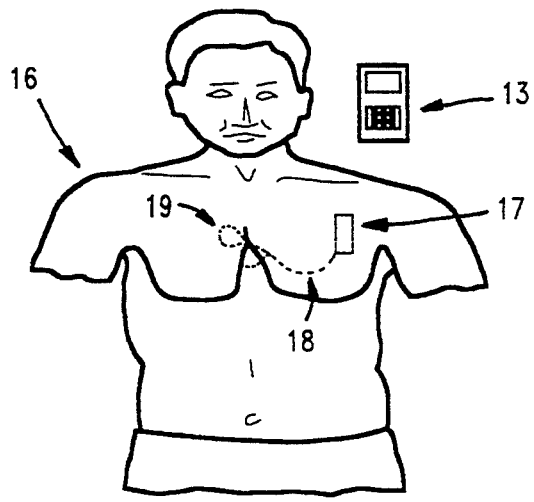
FIG. 1  FIG. 2
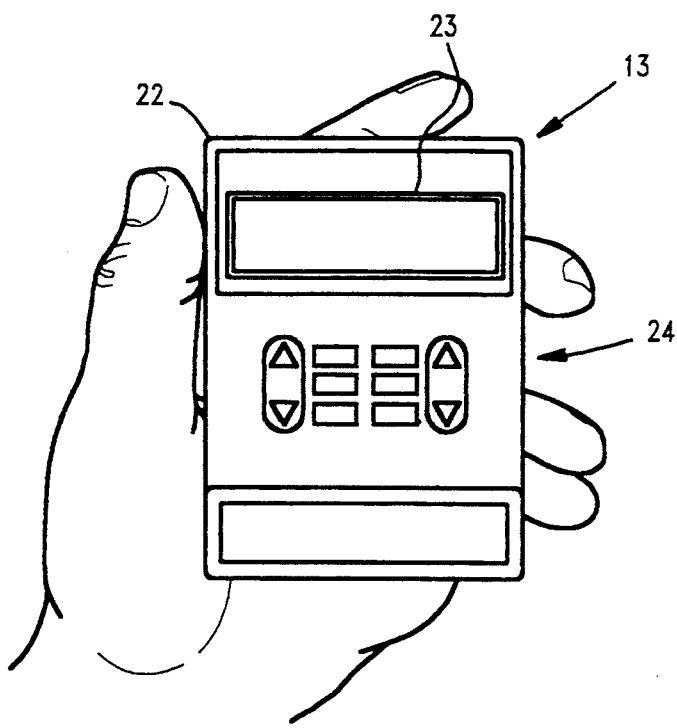
FIG. 3

STORAGE INTERROGATION APPARATUS FOR CARDIAC DATA

BACKGROUND OF THE INVENTION

1. Field of the Invention

The present invention pertains to implantable medical devices, and more particularly to a data transfer and storage apparatus for use with an implanted cardiac device such as a defibrillator or pacemaker.

2. Description of the Prior Art

The cardiac device data acquisition apparatus, commonly referred to as an interrogator, is used by a physician, typically a cardiologist or surgeon, to monitor the program setting of an implanted device and/or to review data acquired from the implanted cardiac device and patient. Some interrogators serve a dual purpose of also transmitting program data to the implanted device and are thus referred to as programmer/interrogators. In the program data transmission situation, the physician sets up detection parameters and/or a mode of therapy for the patient. Both program data transmission and cardiac data acquisition are accomplished by RF communication between the implanted device and the programmer/interrogator through the patient's body.

A primary use of the current generation of interrogator apparatus, or alternatively the monitoring mode of programmer/interrogators is as a follow-up tool to evaluate patient data from an implanted device during subsequent visits to the physician's office. This mode is very important for patients who have an implanted defibrillator as there is no other means available for evaluating the condition or effectiveness of the device. Thus, patients have to schedule frequent periodic visits to their physician's office to have the defibrillator device checked, and also have to make a visit whenever they suspect a cardiac anomaly, such as an arrhythmia. Home follow-up devices and methods which rely on EKG data exist, but such devices and methods are often not suitable for defibrillator patients. The only known home follow-up device suitable for defibrillator patients is manufactured by Applicant's assignee.

The next generation of implantable defibrillators are known to have the additional ability to record continuous electrogram, (EGM) data for limited durations whenever detection circuitry determines that a cardiac event such as an arrhythmia is occurring. However, these devices have limited memory available. The limitation on the available memory in the implanted device is primarily due to the limitation on the physical size of memory chips. Designers strive to make the implantable device smaller, thus limiting storage capacity.

Due to the large memory requirement needed for high resolution analog data when digitized for storage, only short intervals of EKG data can be stored. One such device, Ventritex's Cadence Defibrillator, can store sixty seconds of one event, 32 seconds of each of four events, or 16 seconds of each of seven events. The device always discards the last event data in order to store the most recent event, if the data memory is full.

The longer duration of storage of each event or for a series of events, the better the physician is able to reconstruct the etiology of the patient and device interaction. This is important for optimizing future defibrillator program settings. It is also important for the physician to get as much cardiac event history as possible to better diagnose the patient's condition. These needs are in opposition with a limited amount of memory available in the next generation of implanted devices.

This invention provides an interrogation device and method that may be used by the patient at home to retrieve data from the implanted defibrillator and also to store such data for later transfer and review by the physician. The interrogation device can have up to several orders of magnitude more memory than the implanted device. In use, the patient interrogates the implanted device via the interrogator. The interrogator then stores all new data that had not previously been stored. Data may then be reviewed from the interrogator directly, or communicated from the interrogator to a remote receiving apparatus, for example, via a modem or facsimile. The device and method allow the physician access to many more cardiac event data than could be retrieved from storage from the implanted device alone.

The present invention overcomes the deficiencies of the prior art by providing an interrogator for a implanted cardiac defibrillator whose operating data can be interrogated, stored and electronically relayed by the patient to a physician's office at longer intervals or periods.

SUMMARY OF THE INVENTION

The general purpose of the present invention is a low cost, hand-held interrogator. The device retrieves all available data from the implanted device and stores it in memory. Retrieved data is then shown in a code on the device display, or it can be transmitted through a serial port to a computer terminal or any other display terminal. In one embodiment of the present invention, the interrogator comprises a sealed enclosure including an integral antenna, a receiver and a transmitter, a microprocessor, memory, a double row digital display panel, a plurality of control switches, and a serial input-output port.

In normal usage, the patient holds the device near the implanted defibrillator and initiates an interrogation mode via the control switches. Preferably, the device does not show data, but instead analyzes the data and displays a message to the effect that the transmission is complete and that either all is OK, or to call a physician. A code number may also be included to help the physician identify the nature of the problem. The device holds in memory all of the interrogated data, including stored EGM, so it can be directly retrieved by the physician when a display terminal is later connected to the key-serial port or indirectly via a remote communication process.

In an optional remote communication process and configuration, an auto-dialer/modem, including a well for holding the interrogator, is also supplied to the patient. After interrogating the implanted device and recording the data in its memory, the data is transmitted to the physician at certain time periods or under certain conditions. The patient simply places the interrogator in the holding well of the modem and activates the device. The modem then communicates with the interrogator via RF telemetry, infrared telemetry, or via the serial port, and instructs it to dump its memory. The modem apparatus then calls a preset phone number and transmits the data to a receiving facsimile apparatus or modem in the physician's office.

These and other benefits of this invention will become clear from the following description by reference to the drawings.

BRIEF DESCRIPTION OF DRAWINGS

FIG. 1 illustrates an interrogator in use with a patient having a cardiac defibrillator implanted at the abdominal region and a defibrillation catheter extending therefrom to the heart;

FIG. 2 illustrates an interrogator in use with a patient having a cardiac defibrillator implanted at the pectoral region and a defibrillation catheter extending therefrom to the heart;

FIG. 3 is a front view of the hand held interrogator of the present invention;

DESCRIPTION OF THE PREFERRED EMBODIMENTS

Figure 4:
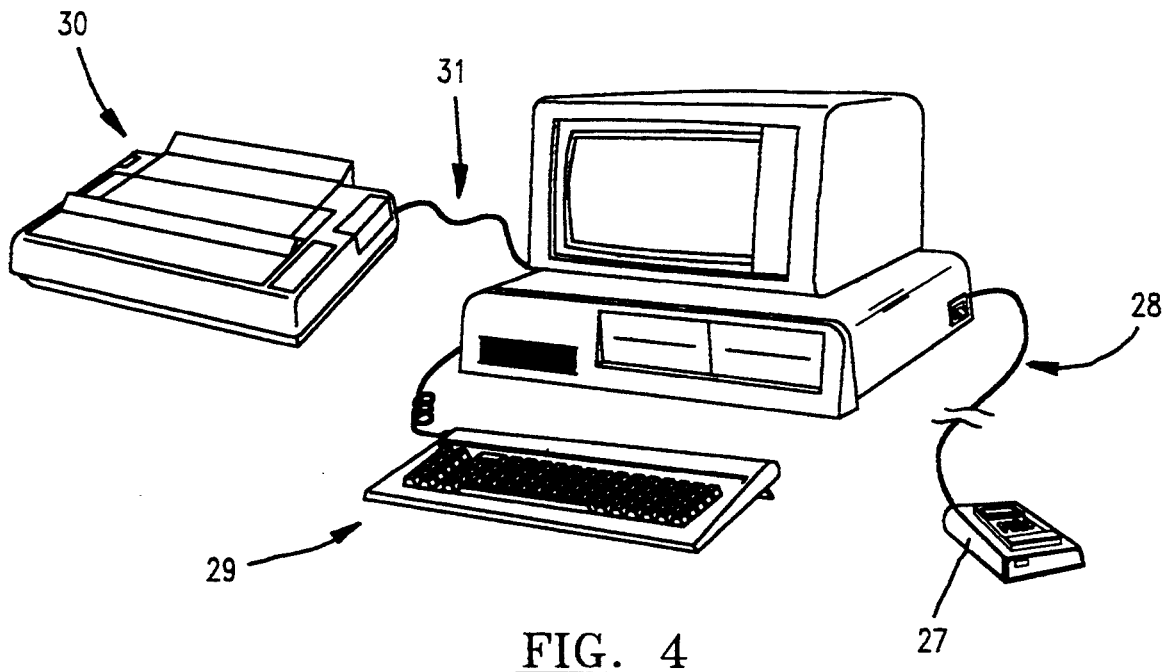
FIG. 4 illustrates the interrogator being utilized to transmit stored data to a remote location via a facsimile process.

This invention provides an interrogation device and method that is used by the patient to retrieve data from an implanted cardiac device and also to store such data for later viewing by the physician. The interrogation device has up to orders of magnitude more memory than the implanted device itself. Each stored event has an identifier tag associated with the data (such as date and time of occurrence) which is transmitted with the data when interrogated. In use, the patient interrogates the implanted device each day and/or whenever they are conscious of an arrhythmia or other cardiac event having occurred. The patient's interrogator then stores all new data that had not previously been stored. The device and method allow the physician access to many more events than could be retrieved from storage from the implanted device alone. After physician review, the interrogator memory is either reset or left in a first-in, first-out mode of discarding the oldest data when its memory is filled.

Referring to FIG. 1, a patient 10 is shown with a cardiac defibrillator 11 implanted in their abdominal region. A defibrillation catheter 12 is shown extending from the defibrillator 11 to the patient's heart via a vascular channel, as is known in the art. As is also well known, the defibrillator 11 comprises a sealed housing enclosing a battery power source, capacitive means, sensing circuity, activation circuity, RF receiving and transmitting circuitry, and catheter connection means. The catheter 12 typically comprises a plurality of insulated conductors, which are connected to defibrillation and pace/sense electrodes located proximate the end of catheter 12 for lodgment in the heart. The primary purpose of the defibrillator system 11, 12 is to deliver a defibrillating charge to the heart upon the detection of a predetermined cardiac event such as an arrhythmia or other life threatening irregularity. A secondary purpose of the defibrillator 11, 12 is to acquire and store electrical signal data from the heart, which are representative of cardiac function and which may be utilized by the diagnostician to determine the health of the heart.

The implanted cardiac defibrillator interrogator 13 is shown disposed near the abdominal region of the body 10 to acquire the stored cardiac function data from the implanted defibrillator 11. Acquisition is accomplished by receiving RF signals transmitted from the defibrillator 11. Defibrillator 11 transmission is initiated by an RF signaling from the interrogator 13.

FIG. 2 shows a cardiac defibrillator 17 implanted in the pectoral region of a patient 16 and having a cardiac catheter 18 extending transvenously to the patient's heart. In addition to the common catheter 18 electrodes, a patch-style defibrillation electrode 19 is shown disposed in the precordial region of the patient 16. The defibrillator 17 and catheter 18 are otherwise configured similar to the implanted defibrillation apparatus 11, 12 shown in FIG. 1. The interrogator 13 is shown operatively positioned for data transfer from the defibrillator 17.

FIG. 3 shows a front view of the implanted cardiac device interrogator 13. The interrogator 13 exterior basically comprises a compact, hand holdable, sealed housing or case 22, a LCD digital display 23, and a plurality of function keys or switches 24. A serial port (not shown) is also disposed on the side or back of the housing 22. The housing 22 encloses the internal electronic circuitry of the interrogator 13. Interrogation program instructions are stored in memory connected to a microprocessor in the internal circuitry interrogator 13. The microprocessor is controlled by the switch pads 24.

The interrogator 13 is controlled by the patient or the physician to allow interrogation of the implanted defibrillator 11 or 17 via the switch pads 24. Interrogation is accomplished by RF communication through the patient's skin by RF circuits in the defibrillator 11 or 17 and in the interrogator 13. The patient can be instructed to view the interrogator display 23 to receive a limited amount of user advisory information.

Figure 5:
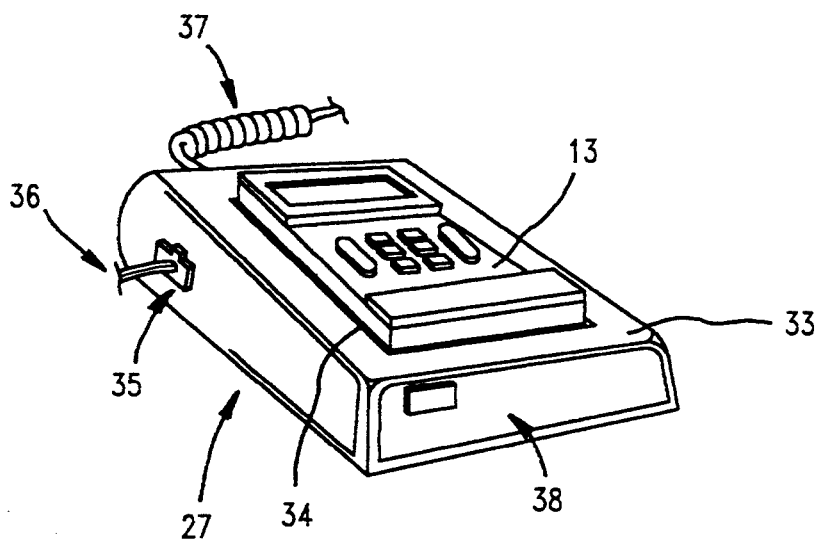
FIG. 5 is a perspective view of the interrogator operatively connected to an auto-dialer/modem apparatus.

FIGS. 4 and 5 illustrate the interrogator 13 in use with an auto-dialer/modem 27. The interrogator 13 is inserted into and is accommodated by a well 34 in the auto-dialer/modem 27. Interrogated data from the implanted device is transmitted from the interrogator 13 memory to the physician upon command from the patient. After communication of memory data, the data in the memory can be dumped so that a new monitoring cycle can then be initiated.

Figure 6:
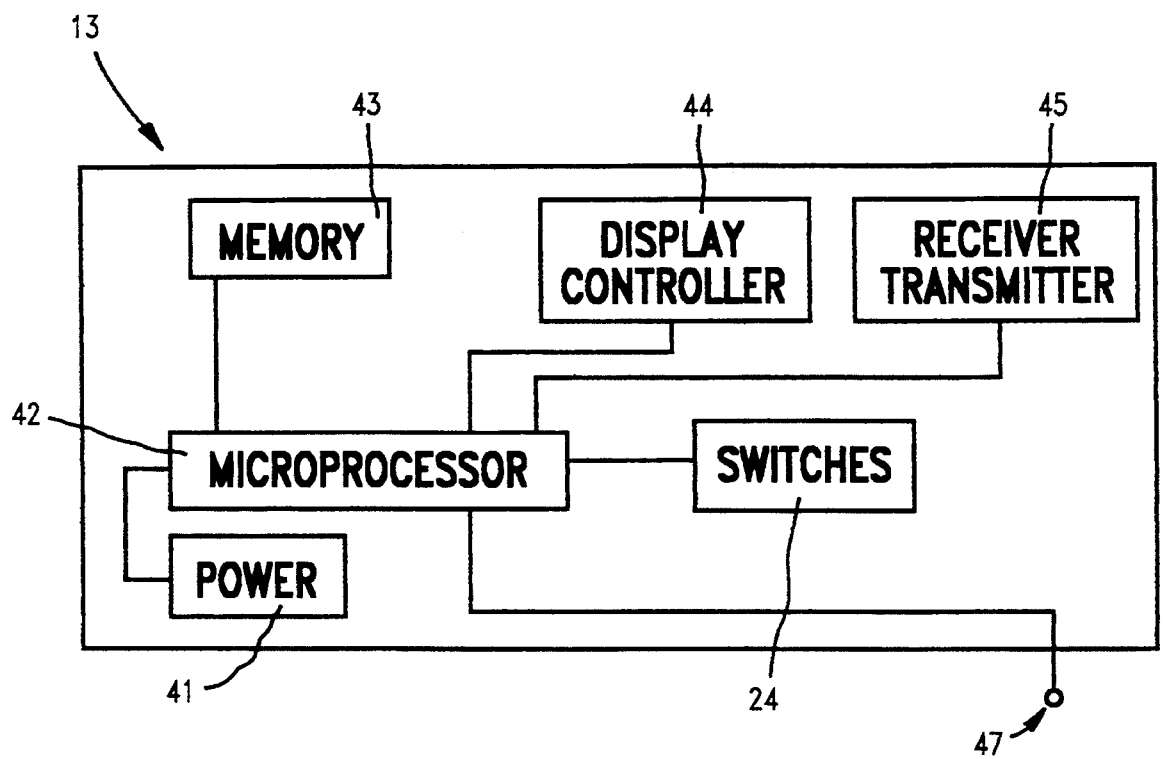
FIG. 6 is a schematic diagram of the interrogator circuitry.

Referring to FIG. 6, the interrogator 13 internal circuitry basically comprises a power supply 41, a microprocessor 42, memory 43, a display controller 44, and a receiver-transmitter section 45. As shown, the microprocessor 42 is connected to the control switches 24. The microprocessor 42 is also shown to be connected to an external serial port 47.

The microprocessor 42 controls the functioning of the device 13. It has an internal memory which stores the program instructions for device function. The microprocessor 42 is preferably a low power processor such as the Motorola 6805 series.

The memory 43 is an integrated circuit attached to the microprocessor 42. The memory 43 is utilized to store the data acquired from the implanted device 11 or 17 until it can be later transmitted to the physician's office. The memory 43 is preferably a combination of several 32K×8K RAM chips such as Intel 512565 series.

In an exemplary use cycle, a week-long, one hour recording of the intervals between heartbeats (R—R intervals) is very beneficial for arrhythmia analysis. Assuming 2 bytes of information storage capacity were required per heartbeat interval, and 86,400 beats per day (at 60 beats per minute), a storage capacity of 172,800 bytes per day would be required. Utilizing still larger memory capacities, continuous recordings of electrograms for later analysis may be provided. At a sample rate of 200 Hz and an 8-bit resolution, this would require 17,280,000 bytes of storage for patient cardiac data pertaining to a single day.

The display controller 44 receives signals from the microprocessor 42 and then activates the proper annunciators on the LCD display 23.

The receiver/transmitter section 45 enables communication with the implanted cardiac device 11 or 17. Data is input from and output to the microprocessor 42. The receiver/transmitter 45 initially signals the implanted device 11 or 17 that a data transfer is to be initiated. The receiver/transmitter 45 then receives the transferred data from the implanted device via RF communication.

In normal usage, each day the patient downloads actual digitized strips of analog electrograms of each "event" that are stored by the implanted device into the external interrogator device 13. These require about 100 samples per second to be stored. In this way, a week's worth of data Is saved for physician analysis. The patient holds the interrogator device 13 near the implanted defibrillator, as shown in FIGS. 1 or 2, and actuates the "interrogator" button. The device preferably does not show data, but instead analyzes the data and displays a message to the effect that the test is completed, and either that all is OK, or to call a physician. The device may also be programmed to provide a code number to help the physician identify the nature of the problem. The device holds in memory all of the interrogated data, including stored EKG's, so it can be retrieved at a later time, as described above.

In the optional configuration shown in FIGS. 4 and 5, the patient is also supplied with the auto-dialer/modem 27. After interrogating the implanted device and recording the data in its memory, the physician or the interrogator device 13 itself may instruct the patient to transmit the data to the physician's office. The patient simply places the interrogator 13 in the holding well 34 of the modem 27 and actuates a "transmit" button 38. The modem device 27 then communicates with the interrogator 13 via RF telemetry or via a serial link and instructs it to dump its memory. The modem device 27 then calls a preset phone number and transmits the data to a receiving modem 29 in the physician's office, via a telephone link 28. A printer 30 is shown connected to a computer 29, with FAX modem circuitry, via link 31. In this manner a facsimile report of the data is generated for immediate review by the diagnostician.

As many changes are possible to the embodiments of this invention utilizing the teachings thereof, the descriptions above, and the accompanying drawings should be interpreted in the illustrative and not the limited sense.

That which is claimed:

1. An interrogation apparatus, for use by a patient, for transmitting information relating to an implanted medical device to a remote location, comprising:
   a. processor means including program control instructions;
   b. means, connected to said processor means, for transmitting and receiving RF signals between said interrogator and the implanted medical device;
   c. an integrated circuit memory for storing signal data received from said implanted medical device, said memory being connected to said processor means and having the capacity to store at least 172 Kbytes of medical device information; and
   d. means to transmit said stored signal data to a location remote from said interrogator, whereby information from the implanted medical device is received in one or more interrogation cycles initiated by the patient and stored, and subsequently transmitted to the remote location.

2. The interrogator apparatus of claim 1, wherein said means for transmitting and receiving signals comprises an RF receiver/transmitter and an antenna.

3. The interrogator apparatus of claim 2, wherein said processor means program control instructions include means for directing said receiver/transmitter to signal the implanted cardiac device to commence a data transmission operation, means for receiving transmitted data therefrom, and means for communicating said received data to said means to store.

4. The interrogator apparatus of claim 1, wherein said means to transmit comprises a serial port.

5. The interrogator apparatus of claim 4, wherein said means to transmit further comprises an external transmitter connected to said serial port.

6. The interrogator apparatus of claim 5, wherein said external transmitter is a modem.

7. The interrogator apparatus of claim 5, wherein said external transmitter comprises means for generating a facsimile.

8. The interrogator apparatus of claim 1, wherein the apparatus is utilized with a cardiac defibrillator implanted medical device with cardiac data acquisition and storage capabilities, said interrogator periodically acquiring and storing cardiac data stored in the implanted cardiac defibrillator.

9. The interrogator apparatus of claim 1, wherein the apparatus is utilized with a cardiac pacemaker implanted medial device with cardiac data acquisition and storage capabilities, said interrogator periodically acquiring and storing cardiac data stored in the implanted cardiac pacemaker.

10. The interrogator apparatus of claim 1, further comprising means to digitally display signal data stored in said interrogator, said means to display being connected to said processor means.

11. The interrogator apparatus of claim 1, further comprising at least one operable input switch connected to said processor means.

12. The interrogator apparatus of claim 1, further comprising power supply means connected to said processor means.

13. A storage interrogation apparatus, for use by a patient, for receiving and storing information from an implanted medical device and for formatting and transmitting a FAX communication report to a remote location, comprising:
   a. a microprocessor for implementing program control instructions;
   b. an RF receiver/transmitter connected to said microprocessor, said RF receiver/transmitter transmitting and receiving signals between said interrogator and the implanted medical device;
   c. an integrated circuit memory for storing signal data received from the implanted medical device, said memory being connected to said microprocessor; and
   d. means to format and transmit a FAX report containing said stored signal data to a location remote from said interrogator, whereby information from the implanted medical device is received in one or more interrogation cycles initiated by the patient and stored, and subsequently incorporated in said FAX report and transmitted to the remote location.

14. A storage interrogation apparatus, for use by a patient, for periodically acquiring and storing cardiac data stored in an implanted cardiac defibrillator and for automatically formatting and transmitting a FAX report to a remote communications system, consisting of:
 a. a microprocessor having and implementing program control instructions;
 b. an RF receiver/transmitter connected to said microprocessor, said RF receiver/transmitter transmitting and receiving signals between said interrogator and said implanted medical device;
 c. an integrated circuit memory for storing signal data received from said implanted medical device, said memory integrated circuit being connected to said microprocessor and having the capacity to store at least 172 Kbytes of information at a sample rate of 200 Hz. and 8-bit resolution;
 d. means to format and transmit a FAX report containing said stored signal data to a location remote from said interrogator;
 e. means to digitally display non-data patient instructions, said means to display being connected to said microprocessor;
 f. a plurality of patient actuatable switches including a first patient switch connected to said microprocessor for controlling the initiation of an interrogation cycle, and a second patient switch connected to said microprocessor for controlling the initiation of a FAX transmission of said FAX report; and
 g. power supply means connected to said microprocessor, whereby the patient initiates an interrogation cycle at a predetermined time, receiving and storing information, by actuating said first patient switch and, based on information presented by said digital display means, initiates a FAX transmission cycle by actuating said second patient switch, thereby transmitting said FAX report to a remote location for analysis.

* * * * *